（12）United States Patent
Vetter et al.

(10) Patent No.: US 7,498,469 B1
(45) Date of Patent: Mar. 3, 2009

(54) COUPLING OF FORMALDEHYDE TO GLYCOALDEHYDE USING N-HETEROCYCLIC CARBENE CATALYSTS

(75) Inventors: Andrew James Vetter, Kingsport, TN (US); Mesfin Ejerssa Janka, Kingsport, TN (US); Joseph Robert Zoeller, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/936,311

(22) Filed: Nov. 7, 2007

(51) Int. Cl.
*C07C 45/72* (2006.01)
(52) U.S. Cl. ...................... 568/458; 568/463
(58) Field of Classification Search .......... 568/458, 568/463
See application file for complete search history.

(56) References Cited

U.S. PATENT DOCUMENTS

| 2,153,064 A | 4/1939 | Larson |
| 4,238,418 A | 12/1980 | Weiss |
| 5,298,668 A | 3/1994 | Gehrer et al. |
| 5,508,422 A | 4/1996 | Teles et al. |
| 5,585,496 A | 12/1996 | Teles et al. |

FOREIGN PATENT DOCUMENTS

GB   508 383   6/1939

OTHER PUBLICATIONS

Matsumoto, Toshihiko et al.; "Selective Formation of Triose from Formaldehyde Catalyzed by Thiazolium Salt"; J. Am. Chem. Soc.; 1984; vol. 106, pp. 4829-4832.
Murata, Kazuhisa et al.; "Role of 1-Methyl-3-Ethylbenzimidazolium Bromide-Ruthenium Catalyst in the One-step Production of Ethylene Glycol via Formaldehyde Condensation and in its Direct Synthesis from Synthesis Gas"; Journal of Molecular Catalysis; 1987; vol. 42; pp. 389-393.
Teles, J. Henrique et al; "The Chemistry of Stable Carbenes"; Helvetica Chimica Acta; 1996; vol. 79; pp. 61-83.
Nyce, Gregory W. et al.; "Expanding the Catalytic Activity of Nucleophilic N-Heterocyclic Carbenes for Transesterification Reactions"; Organic Letters; 2002; pp. 3587-3590; vol. 4, No. 21.

*Primary Examiner*—Sikarl A Witherspoon
(74) *Attorney, Agent, or Firm*—Brett L Nelson; Bernard J. Graves, Jr.

(57) ABSTRACT

Glycoaldehyde (GA) is prepared via self condensation of formaldehyde in the presence of a n-heterocyclic carbene to generate GA and glyceraldehyde (GlyAld) with selectivity toward forming the GA. The carbene is generated in situ by the addition of a base to the salt form of the catalyst. Selectivity is controlled by tuning the active site of the catalyst, either sterically and/or electronically.

14 Claims, No Drawings

COUPLING OF FORMALDEHYDE TO GLYCOALDEHYDE USING N-HETEROCYCLIC CARBENE CATALYSTS

FIELD OF THE INVENTION

This invention pertains to a method for the coupling of formaldehyde (HCHO) to glycoaldehyde (GA) and glyceraldehyde (GlyAld) which employs sterically hindered N-heterocyclic carbenes, formed from the reaction of an imidazolium salt and a base.

BACKGROUND OF THE INVENTION

The coupling of HCHO, though generally run under mild conditions, is difficult to control, often leading to low/poor selectivity to GA (eq. 1). Competing reactions to form GlyAld, C4 and higher sugars (eq. 2), and dihydroxyacetone (DHA), from the aldol condensation of HCHO and GA (eq. 3), contribute to the low selectivity that is generally observed.

1. Condensation of HCHO to glycoaldehyde

2. Condensation of formaldehyde and glycoaldehyde to C3 and higher sugars

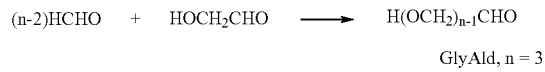

3. Aldol Condensation of formaldehyde and glycoaldehyde

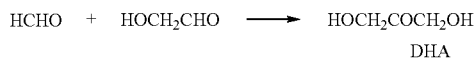

Numerous examples exist in the prior art in which both homogeneous and heterogeneous catalysts have been used to carry out the coupling of HCHO to form GA. The following citations can be used as examples of the existing art in this field: A. H. Weiss, U.S. Pat. No. 4,238,418; J. H. Teles et al., U.S. Pat. Nos. 5,585,496, 5,298,668 and 5,508,422; and J. H. Teles et al. *Helvetica Chimica Acta* 1996, 79, 61.

GA is an attractive C2 material as a precursor to ethylene glycol (EG). The formose reaction provides a simple reaction utilizing formaldehyde as a relatively inexpensive source for making a C2 compound, if the selectivity to C2 can be controlled. GA could then be hydrogenated under relatively mild hydrogenation conditions to EG, an attractive alternative to the known routes using extreme pressures and temperatures (GB 508, 383; U.S. Pat. No. 2,153,064).

Homogeneous triazolium salts, imidazolium salts and thiazolium salts have been used as catalysts for the self-condensation of formaldehyde to GA. The reactions are run under moderate temperatures and ambient pressure, with yields approaching 70% with the triazolium salts as catalysts. In most cases, a significant amount of C3 and higher sugars are seen. In the case of the imidazolium salts, almost no GA is observed (see Teles et al.) with the major product in these reactions being DHA and very poor yields. Low conversion of the HCHO to product can be attributed to the coupling of the imidazolium carbene catalysts used in the reactions, a problem which has been addressed in this invention.

In order to minimize the by-products, a catalyst is needed that selectively makes the C2 GA and does not allow subsequent coupling to occur either by controlling the active site on the catalyst or optimizing the reaction conditions.

BRIEF SUMMARY OF THE INVENTION

A first embodiment according to present invention concerns a process for producing glycoaldehyde. The process comprises contacting an imidazolium salt and a base to form a n-heterocyclic carbene; and contacting said carbene with formaldehyde to form glycoaldehyde. The imidazolium salt is represented by:

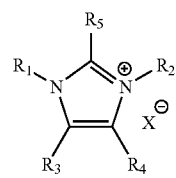

I

Moreover, $R_1$ and $R_2$ are independently selected from the group consisting of alkyl groups having up to 30 carbons, substituted alkyl groups having up to 30 carbons, cycloalkyl groups having about 5 to 30 carbons, substituted cycloalkyl groups having about 5 to 30 carbons, aryl groups having about 6 to 30 carbons, and substituted aryl groups having about 6 to 30 carbons, $R_1$ and $R_2$ being selected so that one molecule of carbene does not couple to a second molecule of carbene, $R_3$ and $R_4$ are independently selected from the group consisting of hydrogen, alkyl groups having up to 30 carbons, substituted alkyl groups having up to 30 carbons, cycloalkyl groups having about 5 to 30 carbons, substituted cycloalkyl groups having about 5 to 30 carbons, aryl groups having 6 to 30 carbons, and substituted aryl groups having about 6 to 30 carbons, $R_5$ is Hydrogen, and X is an anion.

DETAILED DESCRIPTION

According to the present invention, imidazolium carbenes, generated from a combination of their respective salts and a base, have been shown to be successful catalysts in the coupling of formaldehyde to make GA at moderate temperatures and atmospheric pressure. The success of the reactions indicates that the steric bulk of the groups around the active site of the catalyst stabilize the carbene and prevent the carbenes from coupling to each other.

An embodiment of the process described in this invention allows the self condensation of formaldehyde in the presence of a n-heterocyclic carbene to generate GA and GlyAld with selectivity toward forming the GA. The carbene is generated in situ by the addition of a base to the salt form of the catalyst. In another embodiment, the carbene can be pregenerated by the addition of a base to the starting imidazolium salt. The isolated carbene could then be reacted with the formaldehyde source. Selectivity is controlled by tuning the reactivity of the active site of the catalyst, either sterically and/or electronically.

In particular, imidazolium salts (see I below) and a base, such as triethylamine (Et$_3$N), are used in this invention to generate the active carbene catalyst in situ, which catalytically produces moderate yields of the above mentioned products (e.g. GA and GlyAld,) in varying ratios.

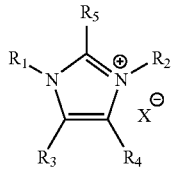

I $R_1$ and $R_2$ are independently selected from alkyl or substituted alkyl groups having up to 30 carbon atoms, cycloalkyl or substituted cycloalkyl groups having about 5 to 30 carbons, or aryl or substituted aryl having about 6 to 30 carbon atoms. $R_1$ and $R_2$ should be carefully selected in order to prevent one molecule of carbene catalyst from coupling to a second molecule of carbene catalyst, see example below (eq. 5). For example, preferred $R_1$ and $R_2$ groups include t-butyl, i-propyl, 2,4,6-trimethylphenyl, 2,6-di-isopropylphenyl, and 4-chlorophenyl.

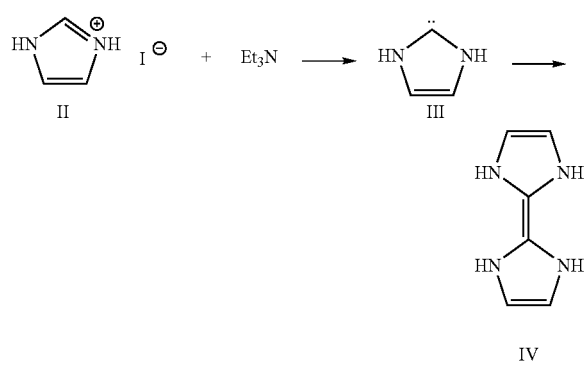

eq. 5

$R_3$ and $R_4$ are independently selected from hydrogen, alkyl or substituted alkyl groups having up to 30 carbon atoms, cycloalkyl or substituted cycloalkyl groups having about 5 to 30 carbons, or aryl or substituted aryl groups having about 6 to 30 carbon atoms. In certain embodiments, the preferred group for these reactions is H.

R5 can be hydrogen, the hydroxymethylene group, the hydroxy-hydroxymethylene-methylidene, and halides, which upon the addition of the base to the imidazolium salt, can be removed to give the active carbene catalyst. For example, R5 can be H for ease of use and catalyst preparation.

X is chosen to neutralize the charge of the imidazolium cation. While the anion choice is not believed to play a critical role in the reaction, preferably, anions of halides such as fluoride, chloride, bromide, or iodide; tetrafluoroborates; tetraphenylborates; nitrates; phosphates; or sulfates are chosen for their ease of use and simple preparation.

The catalyst loading ranges from about 0.001 mol % to about 50.0 mol % with respect to the amount of formaldehyde used. For example, catalyst loading can be from about 0.2 mol % to about 2.0 mol % with respect to the amount of formaldehyde used. At higher catalyst loading, the conversion of formaldehyde to GA and GlyAld increases, however, selectivity to GA decreases. Conversion to GA and GlyAld generally tends to decrease and selectivity to GA increases as catalyst concentration decreases.

In certain embodiments, the preferred process temperature is 80° C. to 120° C.

In another embodiment temperature ranges from 20° C. to 200° C. The reactions are all carried out in the presence of a base, such as $Et_3N$, but any base that does not interfere with the formation of product or distribution of product can be used. A number of bases can be used as bases for activation of the imidazolium salts, including, but not limited to, tertiary amines, polymeric tertiary amines, cyclic amidines, aromatic and nitrogen bases. Suitable tertiary amines are, for example, trimethylamine, triethylamine, tripropylamine, tributylamine, N-methyl piperidine, N-ethyl piperidine, N-propyl piperidine, N-butyl piperidine, cylohexyldiethylamine, and dicyclohexylethylamine. Aromatic bases can be quinoline, pyridine, and N-alkyl imidazoles. Furthermore, inorganic bases, such as alkali metal and alkaline-earth metal bicarbonates, such as alkali metal and alkaline-earth metal carbonates or alkali metal carboxylates, in particular the sodium and potassium salts of C1-C4 carboxylic acids, can be used.

Solvents that are appropriate for the process include alcohols, e.g., methanol, ethanol, propanol, cyclohexanol, 2-ethylhexanol, hydrocarbons, e.g., pentane, hexane, heptane, octane, nonane, decane, cyclohexane, cyclooctane, ureas, e.g., dimethylethylene urea, dimethylpropylene urea, carbonates, e.g., dimethylcarbonate, ethylene carbonate, propylene carbonate, aromatics hydrocarbons, e.g., toluene, xylene, heterocyclic compounds, e.g., pyridine, N-methyl imidazole, M-methylpyrrolidone, ketones, e.g., acetone, esters, e.g., ethyl acetate, ethers, e.g., methyl-tertbutyl ether, diethyl ether, diethylene glycol dimethyl ether, dimethoxyethane, tetrahydrofuran, dioxane, nitrocompounds, e.g., nitrobenzene, nitrotoluene, nitromethane, tertiary amines, e.g., trimethylamine, triethylamine, tripropylamine, halogenated hydrocarbons, e.g., chloroform, dichloromethane, chlorobenzene, dichlorobenzene, sulfoxides, e.g., dimethyl sulfoxide, sulfones, e.g., sulfolane, nitriles, e.g., acetonitrile, propionitrile, butyronitrile, valeronitrile, and amides, e.g., dimethylformamide, dibutylformamide.

An example of a process of making glycoaldehyde according to the present invention is exemplified by the following. A reaction of formaldehyde, as paraformaldehdye or formaldehyde acetal and hemiacetal solutions, trioxane, gaseous formaldehyde or as Formalin is stirred at a temperature ranging from 50 to 200° C., preferably from 75 to 100° C. along with the organic solvent, the catalyst and the base (when the catalyst is generated in situ) from 1 to 250 minutes, preferably from 15 to 60 minutes.

The resulting glycoaldehyde can typically be isolated through extraction or distillation methods.

In an alternative embodiment, the imidazolium salt is attached to a solid surface. For example, the imidazolium salt is attached to microbeads to which the base and other reaction reagents are added. Other suitable solid surfaces include powders, macroporous gels, monoliths and plugs.

Carbenes are known to be air and moisture sensitive which could rapidly lead to catalyst deactivation. It is noted that when run under air-free and moisture-free systems, an increase in yield is often observed.

Representative examples are shown in Table 1.

TABLE 1

Examples of formose chemistry

| Ex. | HCHO Source[a] | Catalyst[b] | Loading (mol %) | Solvent[c] | Temp (° C.) | Time (min) | % HCHO Conversion | % Selectivity to GA |
|---|---|---|---|---|---|---|---|---|
| 1 | paraformaldehyde | A | 0.50 | DMF | 80 | 60 | 22 | 82 |
| 2 | paraformaldehyde | A | 0.50 | DMF | 80 | 240 | 43.5 | 36 |
| 3 | paraformaldehyde | A | 2.00 | DMF | 80 | 60 | 49 | 52 |
| 4 | paraformaldehyde | A | 0.50 | DMF | 80 | 15 | 6 | 88 |
| 5 | paraformaldehyde | A | 2.00 | DMF | 80 | 15 | 19.5 | 71 |
| 6 | paraformaldehyde | A | 0.50 | DMF | 60 | 60 | 5 | 87 |
| 7 | paraformaldehyde | A | 2.00 | DMF | 60 | 60 | 47 | 75 |
| 8 | paraformaldehyde | A | 0.50 | THF | 80 | 60 | 30 | 89 |
| 9 | paraformaldehyde | A | 0.50 | THF | 60 | 60 | 8 | 96 |
| 10 | paraformaldehyde | A | 2.00 | THF | 60 | 60 | 18.5 | 89 |
| 11 | paraformaldehyde | A | 0.50 | EtOAc | 80 | 60 | 39 | 75 |
| 12 | paraformaldehyde | B | 2.00 | DMF | 80 | 15 | 16.5 | 76 |
| 13 | paraformaldehyde | B | 0.50 | DMF | 80 | 60 | 12.5 | 69 |
| 14 | paraformaldehyde | B | 0.50 | DMF | 80 | 240 | 34 | 39 |
| 15 | paraformaldehyde | B | 2.00 | DMF | 80 | 60 | 37 | 45 |
| 16 | paraformaldehyde | B | 2.00 | DMF | 80 | 240 | 50 | 25 |
| 17 | paraformaldehyde | B | 5.00 | DMF | 80 | 15 | 25 | 50 |
| 18 | paraformaldehyde | B | 0.50 | DMF | 80 | 15 | 5 | 87 |
| 19 | paraformaldehyde | B | 2.00 | DMF | 60 | 60 | 9 | 75 |
| 20 | paraformaldehyde | B | 5.00 | DMF | 60 | 60 | 18 | 62 |
| 21 | paraformaldehyde | B | 2.00 | DMF | 60 | 240 | 21 | 53 |
| 22 | paraformaldehyde | B | 0.50 | THF | 80 | 60 | 19 | 91 |
| 23 | paraformaldehyde | B | 2.00 | THF | 80 | 60 | 30 | 85 |
| 24 | paraformaldehyde | C | 5.00 | EtOAc | 80 | 75 | 33.5 | 55 |
| 25 | paraformaldehyde | D | 4.50 | EtOAc | 80 | 75 | <5 | 93 |

[a]Amount of paraformaldehyde charged is 1.0 g.
[b]A = 1,3-bis(2,6-di-iso-propylphenyl)imidazolium chloride, B = 1,3-bis(2,4,6-trimethylphenyl)imidazolium chloride, C = 1,3-bis(2,4,6-trimethylphenyl)-4,5-dihydroimidazolium tetrafluoroborate, D = 1,3-bis(4-chlorophenyl)imidazolium chloride.
[c]DMF—dimethylformamide; THF—tetrahydrofuran; EtOAc—ethyl acetate

EXAMPLES

The process provided by the present invention is further illustrated by the following examples wherein all percentages given are by weight unless specified otherwise.

General. N,N-Dimethylformamide, anhydrous, 98.8%, tetrahydrofuran, anhydrous, 99.9%, ethyl acetate, anhydrous, 99.8% and potassium tert-butoxide were purchased from Aldrich Chemical Company. 1,3-bis(2,6-di-iso-propylphenyl)imidazolium chloride, 95%, 1,3-bis(2,4,6-trimethylphenyl)imidazolium chloride, 95%, 1,3-bis(2,4,6-trimethylphenyl)-4,5-dihydroimidazolium tetrafluoroborate, 95%, and 1,3-bis(4-chlorophenyl)imidazolium chloride, 97% were obtained from Strem Chemicals, Inc. Triethylamine, 99.5% was obtained from Fluka and paraformaldehyde, 90% min from Eastman Kodak Company. All chemicals were used as received.

Reactions were conducted in a Mettler Toledo MultiMax ART 1321490226 equipment (equipped with 4 reactors, stirrers, temperature controlling system, reflux condensers and nitrogen flow) or using a glass pressure vessel under a nitrogen atmosphere.

Analytical. Samples were analyzed by HPLC and UV detection using DNPH derivitization. Agilent 1100; Column: Zorbax Eclipse XDB-C18 3.5 micron 150×4.6 mm (Agilent #963907.902); Solvent: Acetonitrile and water mix; Flow Rate: 1.5 mL/min; Temperature: 50° C.

DNPH reagent Preparation. Prepare a 10 mg/mL dinitrophenylhydrazine reagent by adding 1 g of DNPH to a 100 mL flask. To this add 50 mL of acetonitrile with vibrating until all is dissolved. Add 20 mL of glacial acetic acid, mix and dilute with acetonitrile to 100 mL.

HPLC Sample Preparation. Add 50 µL of the reaction mixture to a 2 dram vial. To this add 900 µL of DNPH reagent. Heat the mixture at 40° C. for 30 min. If solution remains yellow, continue to heat at 40° C. for 30 more min. Add 500 µL of water, mix and inject.

Example 1

A MulitiMax reaction flask equipped with a stir bar and a reflux condenser was charged with 1.0 g (33.0 mmol) of paraformaldehyde and 0.070 g (0.16 mmol, 0.5 mol %) of 1,3-bis(2,6-di-i-propylphenyl)imidazolium chloride. The flask was assembled and purged with nitrogen. Under positive nitrogen flow 40.0 mL of N,N-dimethylformamide and 0.092 mL (0.64 mmol) triethylamine were added. The reaction mixture was heated at 100° C. for 1 h. At the end of the reaction, unreacted paraformaldehyde was removed by filtration and dried. 0.32 g of unreacted dry paraformaldehyde was recovered. The filtrate was analyzed by HPLC and contained 27% of glycolaldehyde, 6% of glyceraldehyde and 67% of formaldehyde. Selectivity of glycolaldehyde in solution is 82%.

Example 2

Procedure was followed as in Example 1 except that the reaction mixture was heated at 80° C. for 4 h. At the end of the reaction, unreacted paraformaldehyde was removed by filtration and dried. 0.18 g of unreacted dry paraformaldehyde was recovered. The filtrate was analyzed by HPLC containing 19% of glycolaldehyde, 34% of glyceraldehyde and 47% of formaldehyde. Selectivity of glycolaldehyde in solution is 36%.

Example 3

Procedure was followed as in Example 1 except that 0.28 g (0.66 mmol, 2.0 mol %) of 1,3-bis(2,6-di-i-propylphenyl) imidazolium chloride catalyst was used. The reaction mixture was heated at 80° C. for 1 h. At the end of the reaction, unreacted paraformaldehyde was removed by filtration and dried. 0.16 g of unreacted dry paraformaldehyde was recovered. The filtrate was analyzed by HPLC containing 30% of glycolaldehyde, 28% of glyceraldehyde and 42% of formaldehyde. Selectivity of glycolaldehyde in solution is 52%.

Example 4

Procedure was followed as in Example 1 except that the reaction mixture was heated at 80° C. for 25 min. At the end of the reaction, unreacted paraformaldehyde was removed by filtration and dried. 0.60 g of unreacted dry paraformaldehyde was recovered. The filtrate was analyzed by HPLC containing 14% of glycolaldehyde, 2% of glyceraldehyde and 84% of formaldehyde. Selectivity of glycolaldehyde in solution is 88%.

Example 5

Procedure was followed as in Example 1 except that 0.28 g (0.66 mmol, 2.0 mol %) of 1,3-bis(2,6-di-i-propylphenyl) imidazolium chloride catalyst was used. The reaction mixture was heated at 80° C. for 25 min. At the end of the reaction, unreacted paraformaldehyde was removed by filtration and dried. 0.37 g of unreacted dry paraformaldehyde was recovered. The filtrate was analyzed by HPLC containing 22% of glycolaldehyde, 9% of glyceraldehyde and 69% of formaldehyde. Selectivity of glycolaldehyde in solution is 71%.

Example 6

Procedure was followed as in Example 1 except that the reaction mixture was heated at 60° C. for 1 h. At the end of the reaction, unreacted paraformaldehyde was removed by filtration and dried. 0.73 g of unreacted dry paraformaldehyde was recovered. The filtrate was analyzed by HPLC containing 17% of glycolaldehyde, 2.5% of glyceraldehyde and 80.5% of formaldehyde. Selectivity of glycolaldehyde in solution is 87%.

Example 7

Procedure was followed as in Example 1 except that 0.28 g (0.66 mmol, 2.0 mol %) of 1,3-bis(2,6-di-i-propylphenyl) imidazolium chloride catalyst was used. The reaction mixture was heated at 60° C. for 1 h. At the end of the reaction, unreacted paraformaldehyde was removed by filtration and dried. 0.10 g of unreacted dry paraformaldehyde was recovered. The filtrate was analyzed by HPLC containing 39% of glycolaldehyde, 13% of glyceraldehyde and 48% of formaldehyde. Selectivity of glycolaldehyde in solution is 75%.

Example 8

Procedure was followed as in Example 1 except that 40.0 mL of THF were used as the solvent. The reaction mixture was heated at 80° C. for 1 h. At the end of the reaction, unreacted paraformaldehyde was removed by filtration and dried. 0.43 g of unreacted dry paraformaldehyde was recovered. The filtrate was analyzed by HPLC containing 46% of glycolaldehyde, 6% of glyceraldehyde and 48% of formaldehyde. Selectivity of glycolaldehyde in solution is 89%.

Example 9

Procedure was followed as in Example 1 except that the reaction mixture was heated at 60° C. for 1 h and THF was used as the solvent. At the end of the reaction, unreacted paraformaldehyde was removed by filtration and dried. 0.85 g of unreacted dry paraformaldehyde was recovered. The filtrate was analyzed by HPLC containing 52% of glycolaldehyde, 2% of glyceraldehyde and 46% of formaldehyde. Selectivity of glycolaldehyde in solution is 96%.

Example 10

Procedure was followed as in Example 1 except that 0.28 g (0.66 mmol, 2.0 mol %) of 1,3-bis(2,6-di-i-propylphenyl) imidazolium chloride catalyst was used and THF was used as the solvent. The reaction mixture was heated at 60° C. for 1 h in 40.0 mL of THF. At the end of the reaction, unreacted paraformaldehyde was removed by filtration and dried. 0.73 g of unreacted dry paraformaldehyde was recovered. The filtrate was analyzed by HPLC containing 61% of glycolaldehyde, 7.5% of glyceraldehyde and 31.5% of formaldehyde. Selectivity of glycolaldehyde in solution is 89%.

Example 11

Procedure was followed as in Example 1 except that the reaction mixture was heated at 80° C. for 1 h in 40.0 mL of EtOAc. At the end of the reaction, unreacted paraformaldehyde was removed by filtration and dried. 0.46 g of unreacted dry paraformaldehyde was recovered. The filtrate was analyzed by HPLC containing 55% of glycolaldehyde, 18% of glyceraldehyde and 27% of formaldehyde. Selectivity of glycolaldehyde in solution is 75%.

Example 12

Procedure was followed as in Example 1 except that 0.22 g (0.66 mmol, 2.0 mol %) of 1,3-bis(2,4,6-trimethylphenyl) imidazolium chloride catalyst was used. The reaction mixture was heated at 80° C. for 25 min. At the end of the reaction, unreacted paraformaldehyde was removed by filtration and dried. 0.21 g of unreacted dry paraformaldehyde was recovered. The filtrate was analyzed by HPLC containing 16% glycolaldehyde, 5% glyceraldehyde and 79% formaldehyde. Selectivity to glycolaldehyde in solution is 76%.

Example 13

Procedure was followed as in Example 12 except that 0.056 g (0.165 mmol, 0.5 mol %) of 1,3-bis(2,4,6-trimethylphenyl) imidazolium chloride catalyst was used. The reaction mixture was heated at 80° C. for 1 h. At the end of the reaction, unreacted paraformaldehyde was removed by filtration and dried. 0.22 g of unreacted dry paraformaldehyde was recovered. The filtrate was analyzed by HPLC containing 11% of glycolaldehyde, 5% of glyceraldehyde and 84% of formaldehyde. Selectivity of glycolaldehyde in solution is 69%.

Example 14

Procedure was followed as in Example 12 except that the reaction mixture was heated at 80° C. for 4 h. At the end of the reaction, unreacted paraformaldehyde was removed by filtration and dried. 0.18 g of unreacted dry paraformaldehyde was recovered. The filtrate was analyzed by HPLC containing 16% of glycolaldehyde, 25% of glyceraldehyde and 59% of formaldehyde. Selectivity of glycolaldehyde in solution is 39%.

Example 15

Procedure was followed as in Example 12 except that the reaction mixture was heated at 80° C. for 25 min. At the end of the reaction, unreacted paraformaldehyde was removed by filtration and dried. 0.16 g of unreacted dry paraformaldehyde was recovered. The filtrate was analyzed by HPLC containing 20% of glycolaldehyde, 24% of glyceraldehyde and 56% of formaldehyde. Selectivity of glycolaldehyde in solution is 45%.

Example 16

Procedure was followed as in Example 12 except that the reaction mixture was heated at 80° C. for 4 h. At the end of the reaction, unreacted paraformaldehyde was removed by filtration and dried. 0.16 g of unreacted dry paraformaldehyde was recovered. The filtrate was analyzed by HPLC containing 15% of glycolaldehyde, 45% of glyceraldehyde and 40% of formaldehyde. Selectivity of glycolaldehyde in solution is 25%.

Example 17

Procedure was followed as in Example 12 except that 0.56 g (1.65 mmol, 5.0 mol %) of 1,3-bis(2,4,6-trimethylphenyl)imidazolium chloride catalyst was used. The reaction mixture was heated at 80° C. for 1 h. At the end of the reaction, unreacted paraformaldehyde was removed by filtration and dried. 0.26 g of unreacted dry paraformaldehyde was recovered. The filtrate was analyzed by HPLC containing 17% of glycolaldehyde, 17% of glyceraldehyde and 66% of formaldehyde. Selectivity of glycolaldehyde in solution is 50%.

Example 18

Procedure was followed as in Example 1 except that 0.056 g (0.16 mmol, 0.5 mol %) of 1,3-bis(2,4,6-trimethylphenyl)imidazolium chloride catalyst was used. The reaction mixture was heated at 80° C. for 25 min. At the end of the reaction, unreacted paraformaldehyde was removed by filtration and dried. 0.54 g of unreacted dry paraformaldehyde was recovered. The filtrate was analyzed by HPLC containing 10% of glycolaldehyde, 1.5% of glyceraldehyde and 88.5% of formaldehyde. Selectivity of glycolaldehyde in solution is 87%.

Example 19

Procedure was followed as in Example 12 except that the reaction mixture was heated at 60° C. for 1 h. At the end of the reaction, unreacted paraformaldehyde was removed by filtration and dried. 0.54 g of unreacted dry paraformaldehyde was recovered. The filtrate was analyzed by HPLC containing 15% of glycolaldehyde, 5% of glyceraldehyde and 80% of formaldehyde. Selectivity of glycolaldehyde in solution is 75%.

Example 20

Procedure was followed as in Example 12 except that 0.56 g (1.65 mmol, 5.0 mol %) of 1,3-bis(2,4,6-trimethylphenyl) imidazolium chloride catalyst was used. The reaction mixture was heated at 60° C. for 1 h. At the end of the reaction, unreacted paraformaldehyde was removed by filtration and dried. 0.32 g of unreacted dry paraformaldehyde was recovered. The filtrate was analyzed by HPLC containing 16% of glycolaldehyde, 10% of glyceraldehyde and 74% of formaldehyde. Selectivity of glycolaldehyde in solution is 62%.

Example 21

Procedure was followed as in Example 12 except that the reaction mixture was heated at 60° C. for 4 h. At the end of the reaction, unreacted paraformaldehyde was removed by filtration and dried. 0.18 g of unreacted dry paraformaldehyde was recovered. The filtrate was analyzed by HPLC containing 13.5% of glycolaldehyde, 12% of glyceraldehyde and 74.5% of formaldehyde. Selectivity of glycolaldehyde in solution is 53%.

Example 22

Procedure was followed as in Example 12 except that 0.056 g (0.16 mmol, 0.5 mol %) of 1,3-bis(2,4,6-trimethylphenyl) imidazolium chloride catalyst was used. The reaction mixture was heated at 80° C. for 1 h in 40.0 mL of THF. At the end of the reaction, unreacted paraformaldehyde was removed by filtration and dried. 0.54 g of unreacted dry paraformaldehyde was recovered. The filtrate was analyzed by HPLC containing 38% of glycolaldehyde, 4% of glyceraldehyde and 58% of formaldehyde. Selectivity of glycolaldehyde in solution is 91%.

Example 23

Procedure was followed as in Example 12 except that the reaction mixture was heated at 80° C. for 1 h in 40.0 mL of THF. At the end of the reaction, unreacted paraformaldehyde was removed by filtration and dried. 0.42 g of unreacted dry paraformaldehyde was recovered. The filtrate was analyzed by HPLC containing 44% of glycolaldehyde, 8% of glyceraldehyde and 48% of formaldehyde. Selectivity of glycolaldehyde in solution is 85%.

Example 24

A glass pressure vessel was charged with 1.0 g (33.0 mmol) of paraformaldehyde and 0.656 g (1.65 mmol, 5.0 mol %) of 1,3-bis(2,4,6-trimethylphenyl)-4,5-dihydroimidazolium tetrafluoroborate. To this was added 15.5 mol EtOAc and 232 μL (1.65 mmol) of $Et_3N$. The reaction mixture was heated at 80° C. for 1 h. At the end of the reaction, unreacted paraformaldehyde was removed by filtration and dried. 0.5 g of unreacted paraformaldehyde was recovered. The filtrate was analyzed by HPLC containing 37% of glycolaldehyde, 30% of glyceraldehyde and 33% of formaldehyde. Selectivity of glycolaldehyde in solution is 55%.

Example 25

A glass pressure vessel was charged with 1.0 g (33.0 mmol) of paraformaldehyde and 0.490 g (1.5 mmol, 4.5 mol %) of 1,3-bis(4-chlorophenyl)imidazolium chloride. To this was added 15.5 mol EtOAc and 232 μL (1.65 mmol) of $Et_3N$. The reaction mixture was heated at 80° C. for 1 h. At the end of the reaction, unreacted paraformaldehyde was removed by filtration and dried. 1.3 g of paraformaldehyde remained, still containing some solvent. The filtrate was analyzed by HPLC containing 46.5% of glycolaldehyde, 3.5% of glyceraldehyde and 50% of formaldehyde. Selectivity of glycolaldehyde in solution is 93%.

The invention has been described in detail with particular reference to preferred embodiments thereof, but it will be understood that variations and modifications can be effected within the spirit and scope of the invention.

We claim:

1. A process for producing glycoaldehyde comprising:
   contacting an imidazolium salt and a base to form a n-heterocyclic carbene; and
   contacting said carbene with formaldehyde to form glycoaldehyde,
   wherein the imidazolium salt is represented by:

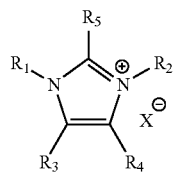

I wherein $R_1$ and $R_2$ are independently substituted aryl groups having about 6 to 30 carbons,
$R_3$ and $R_4$ are independently selected from the group consisting of hydrogen, alkyl groups having up to 30 carbons, substituted alkyl groups having up to 30 carbons, cycloalkyl groups having about 5 to 30 carbons, substituted cycloalkyl groups having about 5 to 30 carbons, aryl groups having 6 to 30 carbons, and substituted aryl groups having about 6 to 30 carbons,
$R_5$ is selected from the group consisting of hydrogen, a hydroxymethylene, a hydroxy-hydroxymethylene-methylidene, and a halide, and
X is an anion; and
wherein selectivity to glycoaldehyde is at least about 25%.

2. The process according to claim 1, wherein $R_3$ and $R_4$ are hydrogen.

3. The process according to claim 1, wherein $R_5$ is hydrogen.

4. The process according to claim 1, wherein X is fluoride, chloride, bromide, or iodide.

5. The process according to claim 1, wherein X is a tetrafluoroborate, a tetraphenylborate, a nitrate, a phosphate, or a sulfate.

6. The process according to claim 1, wherein the imidazolium salt I is present in an amount from about 0.001 mol % to about 50.0 mol % with respect to an amount of the formaldehyde.

7. The process according to claim 6, wherein the imidazolium salt I is present in an amount from about 0.2 mol % to about 2.0 mol % with respect to an amount of the formaldehyde.

8. The process according to claim 1, wherein the process is carried out at a temperature of about 20° C. to about 200° C.

9. The process according to claim 8, wherein the temperature is about 80° C. to about 120° C.

10. The process according to claim 1, wherein the base is a tertiary amine, a polymeric tertiary amine, a cyclic amidine, an aromatic base, a nitrogen base, or a combination thereof.

11. The process according to claim 10, wherein the tertiary amine is a trimethylamine, a triethylamine, a tripropylamine, a tributylamine, a N-methyl piperidine, a N-ethyl piperidine, a N-propyl piperidine, a N-butyl piperidine, a cylohexyldiethylamine, a dicyclohexylethylamine, or a combination thereof.

12. The process according to claim 1, further comprising isolating said glycoaldehyde.

13. The process according to claim 1, wherein the imidazolium salt is attached to a solid surface.

14. The process according to claim 13, wherein said solid surface is a microbead, a powder, a macroporous gel, a monolith, or a plug.

* * * * *